US010401356B2

(12) United States Patent
Uehara (10) Patent No.: US 10,401,356 B2
(45) Date of Patent: Sep. 3, 2019

(54) ANALYTE-MEASURING SENSOR (71) Applicant: JNC CORPORATION, Tokyo (JP)

(72) Inventor: Nobuo Uehara, Tochigi (JP)

(73) Assignee: JNC CORPORATION, Tokyo (JP)

( * ) Notice: Subject to any disclaimer, the term of this patent is extended or adjusted under 35 U.S.C. 154(b) by 28 days.

(21) Appl. No.: 14/425,325

(22) PCT Filed: Sep. 4, 2013

(86) PCT No.: PCT/JP2013/073782
§ 371 (c)(1),
(2) Date: Jul. 5, 2015

(87) PCT Pub. No.: WO2014/038585
PCT Pub. Date: Mar. 13, 2014

(65) Prior Publication Data
US 2015/0293081 A1    Oct. 15, 2015

(30) Foreign Application Priority Data

Sep. 4, 2012 (JP) ................................ 2012-194085

(51) Int. Cl.
*G01N 33/545* (2006.01)
*G01N 33/553* (2006.01)
*G01N 33/543* (2006.01)
*G01N 33/532* (2006.01)
*G01N 33/58* (2006.01)

(52) U.S. Cl.
CPC ......... *G01N 33/545* (2013.01); *G01N 33/532* (2013.01); *G01N 33/54326* (2013.01); *G01N 33/54333* (2013.01); *G01N 33/54393* (2013.01); *G01N 33/553* (2013.01); *G01N 33/587* (2013.01)

(58) Field of Classification Search
CPC ............... G01N 33/545; G01N 33/532; G01N 33/54326; G01N 33/54393; G01N 33/54333; G01N 33/553; G01N 33/587
See application file for complete search history.

(56) References Cited

U.S. PATENT DOCUMENTS

| 7,846,412 | B2 | 12/2010 | Nie et al. | |
|---|---|---|---|---|
| 8,313,777 | B2 | 11/2012 | Maitra et al. | |
| 8,715,741 | B2 | 5/2014 | Maitra et al. | |
| 8,993,487 | B2 | 3/2015 | Yoo | |
| 2005/0175702 | A1* | 8/2005 | Muller-Schulte | A61K 41/00 424/486 |
| 2007/0148437 | A1* | 6/2007 | Muller-Schulte | A61K 9/0009 428/327 |
| 2008/0241964 | A1 | 10/2008 | Kaieda et al. | |
| 2009/0001025 | A1* | 1/2009 | Takahashi | G01N 27/745 210/695 |
| 2009/0190135 | A1* | 7/2009 | Clarizia | C12N 5/0068 356/432 |
| 2011/0059441 | A1 | 3/2011 | Pelton et al. | |
| 2011/0104261 | A1 | 5/2011 | Drummond et al. | |

FOREIGN PATENT DOCUMENTS

| CN | 101166834 | 4/2008 |
|---|---|---|
| CN | 101421623 | 4/2009 |
| CN | 101583379 | 11/2009 |
| CN | 102206351 | 10/2011 |
| EP | 2009442 | 12/2008 |
| EP | 2037272 | 3/2009 |
| JP | 2008-268186 | 11/2008 |
| JP | 2010-066200 | 3/2010 |
| JP | 2010-197046 | 9/2010 |
| WO | 2008/124936 | 10/2008 |
| WO | 2010/137532 | 12/2010 |

OTHER PUBLICATIONS

Escubed, Zeta Potential, 2009, 2 pages, retrieved from http://www.escubed.co.uk/sites/default/files/zeta_potential_(an011)_elecrophoresis.pdf on May 1, 2016.*
Zeta-Meter, Zeta Potential: A complete course in 5 minutes, 8 pages, 1997, retrieved from http://www.zeta-meter.com/5min.pdf on May 1, 2016.*
"The Extended European Search Report of European Counterpart Application", dated Mar. 14, 2016, pp. 1-8.
"International Search Report (Form PCT/ISA/210)", dated Dec. 10, 2013, with English translation thereof, pp. 1-2.
"Office Action of China Counterpart Application", dated Dec. 3, 2015, pp. 1-11, with English translation thereof.
"Office Action of China Counterpart Application" with English translation thereof, dated Jun. 20, 2016, p. 1-p. 10.
Shimada et al., "Blue-to-Red Chromatic Sensor Composed of Gold Nanoparticles Conjugated with Thermoresponsive Copolymer for Thiol Sensing", Langmuir, Sep. 29, 2007, pp. 11225-11232.

* cited by examiner

*Primary Examiner* — Andrea S Grossman
(74) *Attorney, Agent, or Firm* — JCIPRNET (57) ABSTRACT

An object of the present invention is to provide an analyte-measuring sensor using a thermoresponsive polymer, which is a novel analyte-measuring sensor capable of quantitatively measuring a target analyte with higher sensitivity. The analyte-measuring sensor of the present invention comprises a labeled particle capable of specifically reacting with a measurement target analyte, a thermoresponsive polymer, a charged substance exhibiting a positive or negative zeta potential in a solution, and a metal particle, and said metal particle is coated with a copolymer of said labeled particle, said charged substance and said thermoresponsive polymer.

7 Claims, 8 Drawing Sheets

[Transmittance of Analyte-Measuring Sensor 1]

*Fig. 2(b)*

[Transmittance of Analyte-Measuring Sensor 2]

Fig. 3(a) [Transmittance of Analyte-Measuring Sensor 3]

Fig. 3(b) [Transmittance of Analyte-Measuring Sensor 4]

Fig. 3(c) [Transmittance of Analyte-Measuring Sensor 5]

Fig. 4(a)

[Transmittance of Analyte-Measuring Sensor 6]

Fig. 4(b)

[Transmittance of Analyte-Measuring Sensor 7]

Fig. 4(c)

[Transmittance of Analyte-Measuring Sensor 8]

Fig. 5(a)

[Transmittances of Analyte-Measuring Sensors 3 to 5]

Fig. 5(b)

[Transmittances of Analyte-Measuring Sensors 6 to 8]

Fig. 6

[Transmittances of Each of Solutions]

Fig. 7

[Transmittances of of Analyte-Measuring Sensor 4 in Presence of Bovine Serum]

Fig. 8

[Transmittances of of Analyte-Measuring Sensor 4 in Presence or Absence of Bovine Serum]

ANALYTE-MEASURING SENSOR

CROSS-REFERENCE TO RELATED APPLICATION

This application is a 371 application of the international PCT application serial no. PCT/JP2013/073782, filed on Sep. 4, 2013, which claims the priority benefit of Japan application no. 2012-194085, filed on Sep. 4, 2012. The entirety of each of the abovementioned patent applications is hereby incorporated by reference herein and made a part of this specification.

TECHNICAL FIELD

The present invention relates to an analyte-measuring sensor. More specifically, the present invention relates to an analyte-measuring sensor used for quantitatively determining a measurement target analyte by utilizing an immunoreaction.

BACKGROUND ART

Conventionally, an immunoassay utilizing an immunoreaction has been proposed as a method for detecting or quantitatively determining a trace substance, etc. in the environment. As the general measurement method for the immunoassay, for example, enzyme-linked immunosorbent assay (ELISA) and immunochromatography are known.

These methods require an operation of labeling a biological substance with a fluorescent substance, etc. and therefore, studies are being made on an analyte-measuring sensor that can be more easily and simply produced. For example, there has been proposed a biosensor containing a molecular recognition component capable of specifically reacting with a measurement target analyte, a stimulus-responsive polymer whose volume is changed by a reaction of the measurement target analyte and the molecular recognition component, and a metal particle having an average particle diameter of 0.2 to 200 nm, which varies in the intensity of localized surface plasmon resonance with the volume change of the stimulus-responsive polymer, wherein the metal particle and the molecular recognition component are fixed to the stimulus-responsive polymer (see, for example, Patent Document 1).

CITATION LIST

Patent Document

Patent Document 1: JP-A-2010-197046 (the term "JP-A" as used herein means an "unexamined published Japanese patent application").

SUMMARY OF INVENTION

Technical Problem

In the measurement to quantitatively determine a target analyte by utilizing an immunoreaction, from the viewpoint of practical use, a novel analyte-measuring sensor ensuring sufficient detection sensitivity and easy handling is demanded.

An object of the present invention is to provide an analyte-measuring sensor using a thermoresponsive polymer, which is a novel analyte-measuring sensor capable of quantitatively measuring a target analyte with higher sensitivity.

Solution to Problem

As a result of intensive studies to attain the above-described object, the present inventors have found that when a conjugate is composed of a metal particle, a thermoresponsive polymer, a charged substance exhibiting a positive or negative zeta potential, and a labeled particle capable of specifically reacting with a measurement target analyte, a highly sensitive sensor can be obtained.

That is, the present invention has been achieved by the following (1) to (11).

[1] An analyte-measuring sensor comprising:
   a labeled particle capable of specifically reacting with a measurement target analyte,
   a thermoresponsive polymer,
   a charged substance exhibiting a positive or negative zeta potential in a solution, and
   a metal particle,
wherein said metal particle is coated with a copolymer of said labeled particle, said charged substance and said thermoresponsive polymer.

[2] The analyte-measuring sensor as described in the above [1], wherein an average particle diameter of said metal particle is from 10 to 50 nm.

[3] The analyte-measuring sensor as described in the above [1] or [2], wherein said metal particle is any one metal of gold (Au), silver (Ag), platinum (Pt) and palladium (Pd).

[4] The analyte-measuring sensor as described in any one of the above [1] to [3], wherein said thermoresponsive polymer is at least one of poly(N-isopropylacrylamide) and poly (vinyl methyl ether).

[5] The analyte-measuring sensor as described in any one of the above [1] to [3], wherein said labeled particle is any one member of an antibody, an antigen, peptide, a single-strand DNA, a single-strand RNA, and a derivative thereof.

[6] The analyte-measuring sensor as described in any one of the above [1] to [5], wherein said charged substance exhibits a positive zeta potential in a solution.

[7] The analyte-measuring sensor as described in the above [6], wherein said thermoresponsive polymer has an amino group and said charged substance is an amine-based compound.

[8] The analyte-measuring sensor as described in any one of the above [1] to [7], which contains said labeled particle in an amount of 0.1 to 0.4 mass %.

[9] A method for manufacturing the analyte-measuring sensor described in any one of the above [1] to [8], comprising:
   adding, to a solution containing a monomer for forming a thermoresponsive polymer, a labeled particle capable of specifically reacting with a measurement target analyte and a charged substance exhibiting a positive or negative zeta potential in the solution, thereby causing polymerization and forming a three-component copolymer,
   adding a solution containing a metal particle to the obtained solution containing three-component copolymer, and
   performing heating and cooling to coat said metal particle with said three-component copolymer.

[10] A method for manufacturing the analyte-measuring sensor described in any one of the above [1] to [8], comprising:

adding, to a solution containing a monomer for forming a thermoresponsive polymer, a charged substance exhibiting a positive or negative zeta potential in the solution thereby causing polymerization and forming a copolymer, adding a metal particle to the obtained copolymer to coat said metal particle with said copolymer, and adding a labeled particle capable of specifically reacting with a measurement target analyte to said metal particle-coated copolymer to form a conjugate.

[11] A method for measuring a measurement target analyte, comprising:

in the case where the charged substance of said analyte-measuring sensor exhibits a positive zeta potential, adding a conjugated compound that exhibits a negative zeta potential in a solution and a labeled particle which specifically reacts with a measurement target analyte, or in the case where the charged substance of said analyte-measuring sensor exhibits a negative zeta potential, adding a conjugated compound that exhibits a positive zeta potential in the solution and a labeled particle which specifically reacts with a measurement target analyte, to the analyte-measuring sensor described in any one of the above [1] to [8], and in the case where the thermoresponsive polymer of said analyte-measuring sensor is a thermoresponsive polymer that is insolubilized at a temperature not lower than the lower critical solution temperature to cause phase separation, measuring the transmittance at a temperature not lower than the phase transition temperature of the thermoresponsive polymer of said analyte-measuring sensor, or in the case where the thermoresponsive polymer of said analyte-measuring sensor is a thermoresponsive polymer that is insolubilized at a temperature not higher than the upper critical solution temperature to cause phase separation, measuring the transmittance at a temperature not higher than the phase transition temperature of the thermoresponsive polymer of said analyte-measuring sensor.

Advantageous Effects of Invention

According to the present invention, a measurement target analyte, such as thyroid-stimulating hormone (TSH), thrombin, lectin, concanavalin A and platelet-derived growth factor (PDGF), can be easily and simply measured with high sensitivity. Therefore, the present invention can be effectively utilized, particularly, when detecting a measurement target analyte by utilizing an immunoreaction.

BRIEF DESCRIPTION OF DRAWINGS

FIG. 5 is a view showing the relationship between the avidin concentration and the transmittance at 35° C.

DESCRIPTION OF EMBODIMENTS (Analyte-Measuring Sensor)

The analyte-measuring sensor of the present invention contains a labeled particle capable of specifically reacting with a measurement target analyte, a thermoresponsive polymer, a charged substance exhibiting a positive or negative zeta potential in the solution, and a metal particle.

(Thermoresponsive Polymer)

The thermoresponsive polymer is a polymer whose physical properties vary with thermal stimulation, and the solubility in an aqueous solution varies with a temperature change. The thermoresponsive polymer includes a thermoresponsive polymer that dissolves in water at a low temperature but is insolubilized at a temperature not lower than the lower critical solution temperature (abbr. LCST) to cause phase separation, and a thermoresponsive polymer that exhibits water solubility when the temperature rises and exceeds the upper critical solution temperature (abbr. UCST).

The LCST thermoresponsive polymer includes, for example, methyl cellulose, polyethylene oxide, saponified polyvinyl acetate, poly(vinyl methyl ether) (abbr. PMVE), poly(N-isopropylacrylamide) (abbr. PNIPAM), and hydroxypropyl cellulose. The UCST thermoresponsive polymer includes, for example, poly(acryloylglycineamide), poly(acryloylasparagineamide), poly(acryloylglutamineamide), and a copolymer of acryloylglycineamide and acryloylasparagineamide.

Poly(N-isopropylacrylamide) has LCST around 32° C. and undergoes a very sharp change of phase transition. Since this LCST is a temperature relatively close to the body temperature, and poly(N-isopropylacrylamide) exhibits a property of shrinking at LCST or more, the polymer is useful for the preparation of a sustained-release preparation and is utilized in the form of a hydrogel, micell, etc. having a size from nanosize to microsize and capable of encapsulating a drug. The poly(N-isopropylacrylamide) has a hydrogen bonding moiety and swells by carrying water of hydrophobic hydration at a temperature less than LCST. On the other hand, when the temperature rises to LCST or more, the polymer is dehydrated and insolubilized by shrinking into a globular form due to a hydrophobic interaction of the hydrophobic moiety. This phase transition behavior is reversible and therefore, when the temperature drops to less than LCST, the polymer again dissolves in water.

In the present invention, at least one of poly(N-isopropylacrylamide) and poly(vinyl methyl ether) is preferably used as the thermoresponsive polymer. From poly(N-isopropylacrylamide) and poly(vinyl methyl ether), a copolymer having introduced thereinto a monomer having various functional groups can be synthesized by radical copolymerization. This makes it easy to introduce and add a function other than LCST control and thermal response.

The concentration of the thermoresponsive polymer in the analyte-measuring sensor is preferably from 0.01 to 0.02 mass %, more preferably from 0.015 to 0.02 mass %, still more preferably from 0.016 to 0.017 mass %. When the concentration is 0.01 mass % or more, the transmittance advantageously undergoes a distinct change, and when the concentration is 0.02 mass % or less, a distinct change of the transmittance is advantageously maintained.

(Metal Particle)

The metal particle according to the present invention exhibits absorption by surface plasmon resonance (abbr. SPR). The surface plasmon is a plasmon traveling on the metal surface (a plasma wave added with a quantum-mechanical sense). In general, a free electron in a metal is not excited by light and therefore, must be excited by use of an evanescent wave (an electromagnetic wave that attenuates as it goes farther from the metal surface). When the wave number of evanescent wave matches that of the surface plasmon wave, resonance occurs and a phenomenon of attenuation of reflected light is caused.

The metal particle having absorption based on surface plasmon resonance is generally obtained by adjusting the particle diameter of a metal particle to the nm order, but the size may vary depending on the kind of the metal. In the present invention, the average particle diameter of the metal particle is preferably from 10 to 50 nm, more preferably from 10 to 30 nm, still more preferably from 10 to 20 nm. When the average particle diameter is 10 nm or more, the transmittance advantageously undergoes a distinct change, and when the average particle diameter is 50 nm or less, a distinct change of the transmittance is advantageously maintained.

The kind of the metal is not particularly limited, but gold (Au), silver (Ag), platinum (Pt), palladium (Pd), etc. are preferably used. Among these, gold is preferred, because functionality is easily added by surface modification.

The metal particle according to the present invention preferably has an average aspect ratio of 1 to 5. The aspect ratio is a ratio (long axis diameter/short axis diameter) between the length (long axis diameter) and the diameter (short axis diameter) of a particle, and the average aspect ratio is an arithmetic mean value obtained by determining individual aspect ratios of 200 particles. When the average aspect ratio is in the range above, the transmittance advantageously undergoes a distinct change.

The concentration of the metal particle in the analyte-measuring sensor is preferably from 0.01 to 0.02 g/L, more preferably from 0.015 to 0.02 g/L, still more preferably from 0.016 to 0.017 g/L. When the concentration is 0.01 g/L or more, the transmittance advantageously undergoes a distinct change, and when the concentration is 0.02 g/L or less, a distinct change of the transmittance is advantageously maintained.

(Charged Substance)

The charged substance according to the present invention exhibits a positive or negative zeta ($\zeta$) potential in the solution. The zeta potential is defined as the potential at the "slip plane" where a liquid starts flowing in an electric double layer which consists of a fixed ion layer formed around a particle in the solution and an ion diffusion layer. The absolute value of the zeta potential shows a positive or negative value depending on surface characteristics of the particle.

The charged substance is not particularly limited but includes a positively or negatively charged organic substance, etc. Among these, in view of an effective electrostatic interaction, a positively charged organic substance is preferably used.

Examples of the positively charged organic substance include an amine-based compound such as ethylenediamine, diethylenetriamine, triethylenetetramine, tetraethylenepentamine and pentaethylenehexamine, and a derivative thereof. Among these, triethylenetetramine and a derivative thereof are preferred. In the case where the charged substance is an amine-based compound or a derivative thereof, the thermoresponsive polymer comes to have an amino group bearing a positive charge.

Examples of the negatively charged organic substance include a carboxylic acid-based compound such as acrylic acid and methacrylic acid, and a derivative thereof. In the case where the charged substance is a carboxylic acid-based compound or a derivative thereof, the thermoresponsive polymer comes to have a carboxyl group bearing a negative charge.

(Labeled Particle)

The labeled particle according to the present invention is a particle capable of specifically reacting with a measurement target analyte. The labeled particle includes, for example, an antibody, an antigen, peptide, a single-strand DNA, a single-strand RNA, and a derivative thereof. As the specific reaction of the labeled particle (molecular recognition component) with the measurement target analyte, an immunoreaction is known, and when an immunoreaction is utilized, the analyte-measuring sensor can detect the measurement target analyte.

The immunoreaction is a reaction in which an antigen specifically binds with a corresponding antibody and is also called an antigen-antibody reaction. The antibody means a plasma protein that specifically binds with an antigen, i.e., particulate protein. On the other hand, the term "antigen" is used in the wider sense indicating a substance recognizable in the adaptive immune system, and a molecule reacting with an antibody is called an antigen, whereas an antigen which induces antibody production is called an immunogen. The overall structure of the antibody is common to many antibodies and called an immunogloblin (abbr. Ig). Among Ig antibodies, the antibody having the highest population is immunogloblin G (IgG) antibody. In the case of a protein antigen, electrostatic interaction acting between an antigen and an antibody, hydrogen bonding, van der Waals' force, etc. participates in the binding, and the antibody molecule interacts over a wide range with the complementary region on the surface of the antibody which is recognized by the antigen.

Examples of the immunoreaction includes an avidin-biotin interaction. There is very high affinity or discrimination between avidin and biotin.

With regard to the analyte-measuring sensor of the present invention, avidin (molecular weight: about 68 kDa) fulfills the role of an adhesive binding between biotins. Streptavidin (molecular weight: about 60 kDa) derived from *Streptomyces* of actinomycetes is known as a substance having a structure very similar to that of avidin. The streptavidin has an isoelectric point around 6 and does not have a sugar chain, whereas avidin has an isoelectric point around 10 and has a sugar chain. Therefore, streptavidin is less likely to cause non-specific adsorption compared with avidin under physiological conditions and is resistant to denaturation and therefore, this substance can be suitably used.

Biotin is a kind of water-soluble vitamin classified into B vitamins and is also called vitamin $B_7$. In addition, it is sometimes called Coenzyme R from its role played in vivo. Since it is an essential nutrient for humans, a deficiency disease may be caused depending on the intake amount. In the analyte-measuring sensor, biotin is used for labeling a detection target protein and thanks to use of this substance, the antibody can be labeled without impairing physiological activity of the protein. In addition, a plurality of biotins can be covalently bonded to a protein, so that the protein labeled with biotin can interact with a plurality of avidins.

The concentration of the labeled particle in the analyte-measuring sensor is preferably from 0.1 to 0.4 mol %, more preferably from 0.2 to 0.4 mol %, still more preferably from 0.3 to 0.4 mol %. A concentration of 0.1 mol % or more is preferred in view of response to avidin from a low concentration time, and a concentration of 0.4 mol % or less is preferred from the standpoint of maintaining response sensitivity to avidin.

(Production Method of Analyte-Measuring Sensor)

The production method of the analyte-measuring sensor of the present invention is not particularly limited as long as the surface of the metal particle can be coated with a labeled particle capable of specifically reacting with the measurement target analyte and a copolymer of a charged substance and a thermoresponsive polymer. For example, the production method includes, but is not limited to, the following methods 1) to 3):

1) a method where a labeled particle, a charged substance and a monomer for forming a thermoresponsive polymer are copolymerized to synthesize a three-component copolymer (terpolymer) and the three-component copolymer is coated on a metal particle, 2) a method where a monomer for forming a thermoresponsive polymer and a charged substance are copolymerized to synthesize a copolymer and after coating the copolymer on a metal particle, a labeled particle is conjugated therewith, 3) a method where a monomer for forming a thermoresponsive polymer and a charged substance are copolymerized to synthesize a copolymer and a labeled particle is conjugated with the copolymer and then coated on a metal particle.

(Conjugated Compound)

The analyte-measuring sensor of the present invention forms a ternary conjugate together with a measurement target analyte due to the presence of a conjugated compound in the solution. The conjugated compound for use in the present invention is composed of a substance (charged substance) exhibiting a positive or negative zeta potential in the solution and a labeled particle capable of specifically reacting with a measurement target analyte. With regard to the method for measuring a measurement target analyte, in the case where the charged substance of the analyte-measuring sensor exhibits a positive zeta potential, a conjugated compound exhibiting a negative zeta potential in the solution is used, and in the case where the charged substance of the analyte-measuring sensor exhibits a negative zeta potential, a conjugated compound exhibiting a positive zeta potential in the solution is used. The substance exhibiting a positive or negative zeta potential in the solution, which is used for the conjugated compound, is not particularly limited but includes, for example, a polyacrylate. The labeled particle used for the conjugated compound is not particularly limited as long as it can bind to the measurement target analyte, and the labeled particle may be the same as or different from the labeled particle used for the analyte-measuring sensor.

A conjugated compound thus having a zeta potential different from the zeta potential of the charged substance in the analyte-measuring sensor of the present invention is used, whereby the ternary conjugate in the solution is prevented from cancellation of the charge and maintains hydrophilicity. In turn, phase transition does not occur when heated, so that the measurement target analyte can be quantitatively determined by measuring the transmittance of the solution.

(Measurement of Measurement Target Analyte)

The method for measuring a measurement target analyte by using the analyte-measuring sensor obtained above is described below. FIG. 1 is a view for explaining the bonding state of the analyte-measuring sensor, more specifically, FIG. 1A is a view for explaining the state where the analyte-measuring sensor of the present invention is bound to a measurement target analyte, and FIG. 1B is a view for explaining the bonding state of the analyte-measuring sensor when a measurement target analyte is not present.

Figure 1A:
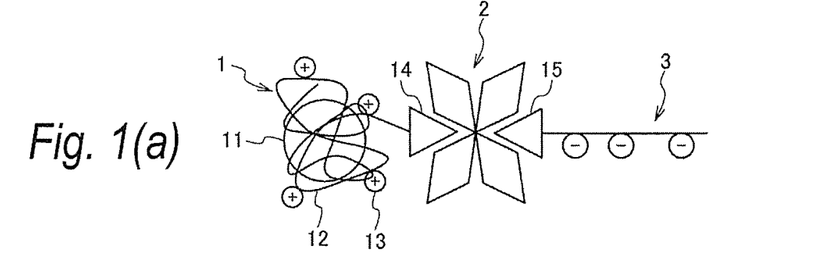
FIG. 1A is a view for explaining the state where the analyte-measuring sensor of the present invention is bound to a measurement target analyte.

With regard to Analyte-Measuring Sensor 1 of the present invention, in the case where a measurement target analyte 2 and a conjugated compound 3 having the same labeled particle 15 as the labeled particle 14 of Analyte-Measuring Sensor 1 are present in the solution, as shown in FIG. 1A, the labeled particle 14 of Analyte-Measuring Sensor 1 and the labeled particle 15 of the conjugated compound 3 interact with the measurement target analyte 2 to form a ternary conjugate. The interaction of the measurement target analyte 2 with the labeled particles 14 and 15 imposes a steric restriction between the charged substance constituting Analyte-Measuring Sensor 1 and the charged substance constituting the conjugated compound 3 and therefore, cancellation of the charge does not completely occur in the conjugate. In turn, the hydrophilicity is maintained, as a result, a definite phase transition is not caused even when heated and the transmittance of the solution does not decrease.

Figure 1B:
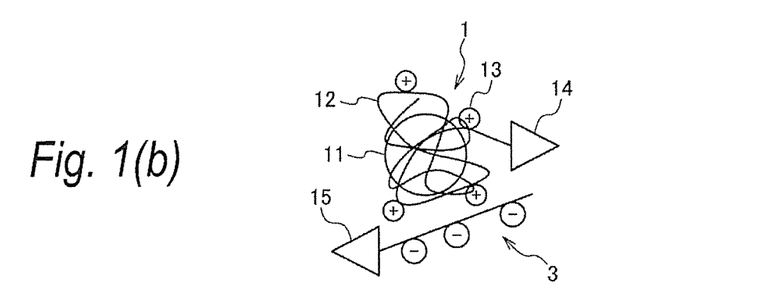
FIG. 1B is a view for explaining the bound state of the analyte-measuring sensor when a measurement target analyte is not present.

On the other hand, in the case where a measurement target analyte 2 is not present, as shown in FIG. 1B, a binary conjugate is formed by electrostatic interaction. When a binary conjugate is formed, efficient cancellation of the charge occurs, as a result, the hydrophilicity is reduced. When the solution in this state is heated at a temperature not lower than the phase transition temperature, a definite phase transition is caused, and the transmittance of the solution decreases.

Under the condition of not lower than the phase transition temperature, the transmittance of the solution varies according to the concentration of the measurement target analyte by the above-described mechanism. In this way, the solution is heated at a temperature not lower than the phase transition temperature, and the transmittance of the solution is measured, whereby the measurement target analyte can be quantitatively determined.

With regard to the method for measuring a measurement target analyte by using the analyte-measuring sensor of the present invention, the analyte can be detected by adding a measurement target analyte and a conjugated compound to the analyte-measuring sensor, adjusting the solution to a temperature not higher than the upper critical solution limit of the thermoresponsive polymer used or to a temperature not lower than the lower critical solution temperature, and measuring the absorbance at a specific wavelength.

For example, in the case of measuring the transmitted light, the analyte-measuring sensor is put in a quartz-made cell, a solution to be measured and a conjugated compound are added thereto, and the change in intensity of the absorption peak at a wavelength of 750 to 900 nm is observed, whereby the transmitted light can be measured.

EXAMPLES

The present invention is described in more detail below by referring to Examples, but the present invention is not limited to these Examples. Incidentally, pure water used was obtained by purifying tap water through a pure water producing apparatus (Model No. F9MN25332C) manufactured by Millipore Corp. and then through Milli-Q Ultrapure Water Production System manufactured by Millipore Corp.
<Apparatus>

The apparatuses used in the present invention are as follows.

Measurement of Absorption Spectrum and Transmittance:

"Model V-650 Ultraviolet-Visible Spectrophotometer" manufactured by JASCO Corp.

DLS Measurement (measurement of particle diameter: the measured value is a harmonic mean particle size (diameter) based on scattered light intensity) and Zeta Potential Measurement:

"Zetasizer Nano ZS" manufactured by Malvern Instruments Ltd. Freeze Drying:

"Model FD-5N Freeze Drier" manufactured by Tokyo Rikakikai Co. Ltd.

Ultrafiltration:

"Model UHP-76K Constant Volume Continuous Filtration Apparatus" manufactured by ADVANTEC Dialysis:

"Cellulose Ester Dialysis Membrane (molecular weight cut off: 10,000)" manufactured by Spectrum Laboratories Inc.

Test Example 1: Synthesis of Analyte-Measuring Sensor

Avidin (Fw: 68,000) was used as the measurement target analyte, and an analyte-measuring sensor was produced by the following method by using a particle composed of gold (Au) as the metal particle, N-isopropylacrylamide (abbr. NIPAAm, Fw: 113.16 (obtained by recrystallizing NIPAAm produced by Wako Pure Chemical Industries, Ltd. by use of hexane (Fw: 86.18)) as the thermoresponsive polymer, a biotin monomer (Fw: 368, N-biotinyl-N'-(meth)acroyltrimethylene amide) as the labeled particle capable of specifically reacting with the measurement target analyte, and triethylenetetramine (abbr. TETA, Fw: 146.24) as the charged substance.

(Preparation of Metal Particle Solution)

Preparation of a metal particle solution was carried out by a citric acid reduction method.

250 mL of 1 mM aqueous tetrachloroaurate solution was put in a 500 mL round-bottomed flask and heated with stirring until just before boiling. After boiling, 25 mL of 38.8 mM aqueous trisodium citrate solution was added, and it was confirmed that the color of the solution changed from pale yellow to deep red. The solution was further heated with stirring for 10 minutes, and then stirring was continued at room temperature for 15 minutes. The solution was suction-filtered using a membrane filter having a pore size of 1 μm, and the gold colloid solution was transferred to a glass reagent bottle and stored in a cold dark place (4° C.) (0.18 g-Au/L, gold colloid solution). The particle diameter of the gold colloid that is a metal particle produced by the method above was about 13 nm.

In addition, a gold colloid solution having a particle diameter of about 30 nm was prepared by changing the amount added of the aqueous trisodium citrate fulfilling the roles as a reducing agent and a dispersant, to 11.6 mL.

(Synthesis of Three-Component Copolymer Composed of Thermoresponsive Polymer, Labeled Particle and Charged Substance)

(1) Synthesis of Copolymer, i.e., Poly(N-Isopropylacrylamide/Acryloyl Triethylenetetramine) (Abbr. Poly(NIPAAm/TETA)) (Hereinafter, Sometimes Referred to as "NIP-TETA")

In advance of polymerization, acryloyl triethylenetetramine (abbr. acTETA) as a reaction intermediate was synthesized according to the following procedure. While stirring a mixed solution of 29.24 g (0.2 mol) of TETA and 200 mL of 1,4-dioxane, which was immersed in ice bath, a mixed solution of 1.72 mL (0.02 mol) of acryloyl chloride (abbr. AC) and 50 mL of 1,4-dioxane was added drop by drop and allowed to react. After the completion of dropwise addition, the white precipitate was separated by filtration, and unreacted AC was removed by washing the precipitate with 1,4-dioxane. The obtained precipitate was dissolved in a small amount of methanol (about 50 mL), and 50 mL of a potassium hydroxide-methanol solution (potassium hydroxide: 1.18 g (0.02 mol)) was added, followed by stirring. The precipitate (KCl) was separated by filtration, and the filtrate containing acTETA was used for copolymerization of the NIPAAm monomer.

To a 500 mL three-neck separable flask, 20.37 g (0.18 mol) of NIPAAm was added so that the feed ratio of monomers (amount of NIP:amount of TETA) can become 90.0:10.0 (ratio by mol). Furthermore, 0.5 mL of 3-mercaptopropionic acid as a polymerization accelerator and 0.3284 g (0.002 mol) of α,α'-azobisisobutyronitrile as a polymerization initiator were added, and polymerization was carried out for 4 hours while heating and stirring at 60° C. by means of an oil bath in a nitrogen atmosphere allowing ventilation to a deoxygenation line using 100 mL of a 5 w/v % pyrogallol-10 w/v % alkali solution (alkali: NaOH). After the completion of polymerization, purification of the polymer was carried out twice by a coprecipitation method using cold diethyl ether. Thereafter, pure water was added to the obtained polymer to make a total volume of 300 mL, and the precipitate was dissolved. The resulting solution was ultrafiltered to 150 mL by using an ultrafiltration membrane with an exclusion limit of 5,000. This operation was carried out 6 times, and a small amount of a standard solution containing carbon disulfide and silver was added to the filtrate. After confirming that the color did not turn to blackish brown, the solution was freeze-dried and stored in a cold dark place. The structural formula of NIP-TETA is shown in the following formula (1):

[Chem. 1]

(1)

of monomers (amount of NIP:amount of TETA:amount of Bio) can become 89.875:10.000:0.125 (ratio by mol), and polymerization was carried out for 4 hours while heating and stirring at 60° C. by means of an oil bath in a nitrogen atmosphere allowing ventilation to a deoxygenation line using 100 mL of a 5 w/v % pyrogallol-10 w/v % alkali solution (alkali: NaOH). After the completion of polymerization, purification of the polymer was carried out twice by a coprecipitation method using cold diethyl ether. Thereafter, pure water was added to the obtained polymer to make a total volume of 300 mL, and the precipitate was dissolved. The resulting solution was ultrafiltered to 60 mL by using an ultrafiltration membrane with an exclusion limit of 5,000. This operation was carried out 6 times, and a small amount of a standard solution containing carbon disulfide and silver was added to the filtrate. After confirming that the color did not turn to blackish brown, the solution was freeze-dried and stored in a cold dark place. The structural formula of NIP-TETA-Bio is shown in the following formula (2):

[Chem. 2]

(2)

(2) Synthesis of Three-Component Copolymer, i.e., Poly(N-Isopropylacrylamide/Acryloyl Triethylenetetramine/Acryloyl-Biotin) (Abbr. Poly(NIPAAm/TETA/Bio)) (Hereinafter, Sometimes Referred to as "NIP-TETA-Bio")

acTETA was synthesized in the same manner on a ⅕-fold scale of (1) Synthesis of NIP-TETA. The obtained acTETA was used for the copolymerization of an NIP monomer and a biotin monomer.

A 500 mL three-neck separable flask was added with 4.068 g (0.03595 mol) of a NIPAAm monomer (abbr. NIP), 0.0184 g (0.00005 mol) of a biotin monomer, 0.1 mL of 3-mercaptopropionic acid as a polymerization accelerator, and 0.0657 g (0.0004 mol) of α,α'-azobisisobutyronitrile as a polymerization initiator were added so that the feed ratio

(Preparation of Analyte-Measuring Sensor: Analyte-Measuring Sensor 1)

To a 50 mL measuring flask, 6.25 mL of a 2.0 mass % NIP-TETA-Bio solution and 15 mL of a 0.18 g-Au/L metal particle solution (particle diameter: about 13 nm) were added and diluted with pure water to adjust the volume to 50 mL.

The resulting solution was heated at 90° C. for 30 minutes by means of a water bath, cooled at 0° C. for 30 minutes by means of an ice bath, and stirred. This operation was repeated three times. The obtained solution was put in a cellophane tube with a molecular weight cut off of 10,000, the tube was immersed in a 1 L beaker filled with pure water, and dialysis was carried out for 5 days by replacing the pure water every day.

The synthetic scheme of Analyte-Measuring Sensor 1 is shown in the following formula (3). In the formula, x, y and z respectively represent molar fractions of NIP, TETA and Bio in the polymer.

[Chem. 3]

(3)

(Preparation of Analyte-Measuring Sensor: Analyte-Measuring Sensor 2)

As for a 100 mmol/L biotin solution, this was prepared by dissolving 6.8 mg of biotin-N-hydroxysuccinimide ester (hereinafter, sometimes referred to as "NHS-Biotin") (FW: 341.36, produced by Thermo SCIENTIFIC) in 200 µL of pure water.

To a 50 mL measuring flask, 6.25 mL of a 2.0 mass % NIP-TETA solution and 15 mL of a 0.18 g-Au/L metal particle solution (particle diameter: 13 nm) were added and diluted with pure water to adjust the volume to 50 mL.

The resulting solution was heated at 90° C. for 30 minutes by means of a water bath, cooled at 0° C. for 30 minutes by means of an ice bath, and stirred. This operation was repeated three times to obtain an NIP-TETA-coated metal particle solution (hereinafter, sometimes referred to as "NIP-TETA-Au solution").

To 9 mL of the NIP-TETA-Au solution previously cooled in a 20 mL conical flask, 200 µL of a 100 mmol/L biotin solution prepared by the same method as above was added. The resulting solution was incubated with stirring for 3 hours in an ice bath. The obtained solution was put in a cellophane tube with a molecular weight cut off of 10,000, the tube was immersed in a 1 L beaker filled with pure water, and dialysis was carried out for 5 days by replacing the pure water every day.

The synthetic scheme of Analyte-Measuring Sensor 2 is shown in the following formula (4). In the formula, x and y respectively represent molar fractions of NIP and TETA in the polymer, and p represents the ratio of Bio introduced into TETA.

[Chem. 4]

Test Example 2: Study of Avidin Concentration Affecting Transmittance of Analyte-Measuring Sensor Solution To a 200 mL beaker, 0.8 g (0.014 mol) of sodium chloride, 1.15 g (0.008 mol) of sodium dihydrogenphosphate, 0.2 g (0.003 mol) of potassium chloride, and 0.2 g (0.002 mol) of potassium dihydrogenphosphate were added and dissolved. The resulting solution was diluted with pure water by means of a 100 mL measuring flask to adjust the volume to 100 mL and thereby prepare a phosphate buffered saline (hereinafter, sometimes referred to as "PBS").
(Preparation of Avidin Solution)

A 7.4 μmol/L avidin solution was prepared by dissolving 2.5 mg of avidin in 500 μL of an aqueous 0.01 mol/L sodium dihydrogenphosphate solution.
(Measurement of Transmittance)

The avidin solution having a concentration of 7.4 μmol/L, a 4.4 mg/mL biotinated sodium polyacrylate solution as a conjugated compound, and PBS were added to the analyte-measuring sensor solution prepared above (Analyte-Measuring Sensors 1 and 2), and measurement of temperature transmittance was carried out.

To a quartz-made semi-microcell having a light path length of 1 cm, 300 μL of the analyte-measuring sensor solution, 100 μL of the avidin solution and 50 μL of the biotinated sodium polyacrylate solution were sequentially added. Subsequently, 450 μL of pure water and 100 μL of a PBS solution were added to afford a final liquid amount of 1 mL. The resulting solution was lightly stirred by hand and after each sample solution was made uniform, the transmittance was measured at a wavelength of 850 nm where the metal particle and the thermoresponsive polymer do not have absorption. The measurement conditions are as follows.

Figure 2A:
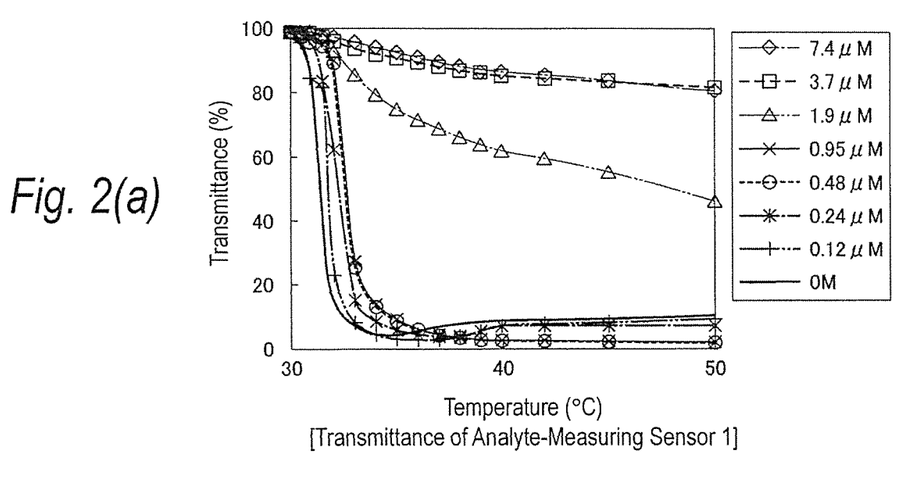
FIG. 2A is a graph showing the relationship between the temperature and the transmittance when the avidin concentration of Analyte-Measuring Sensor 1 is varied.
Figure 2B:
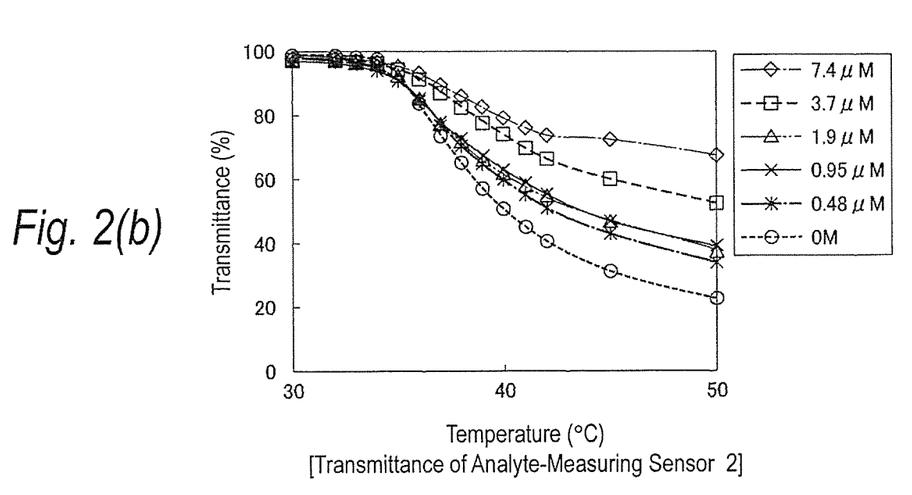
FIG. 2B is a graph showing the relationship between the temperature and the transmittance when the avidin concentration of Analyte-Measuring Sensor 2 is varied.
Figure 3A:
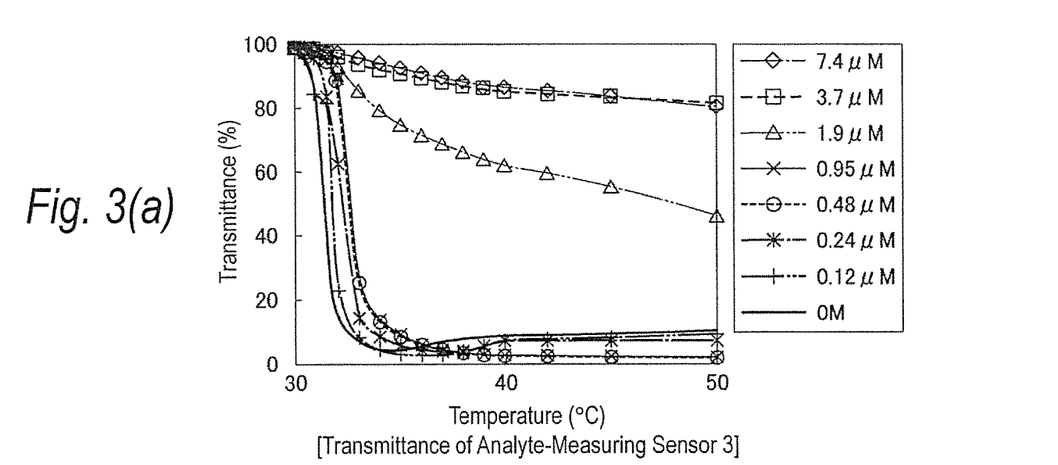
FIG. 3A is a graph showing the relationship between the temperature and the transmittance when the avidin concentration of Analyte-Measuring Sensor 3 is varied.
Figure 3B:
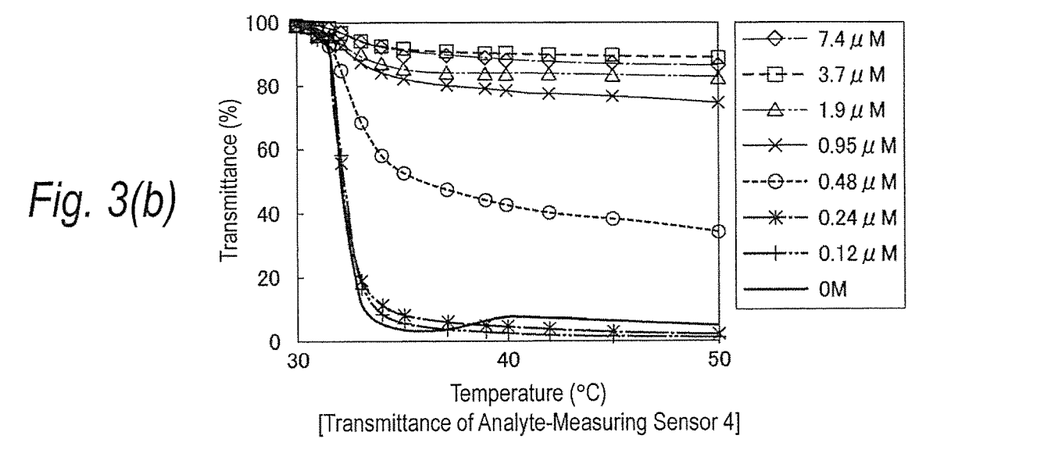
FIG. 3B is a graph showing the relationship between the temperature and the transmittance when the avidin concentration of Analyte-Measuring Sensor 4 is varied.
Figure 3C:
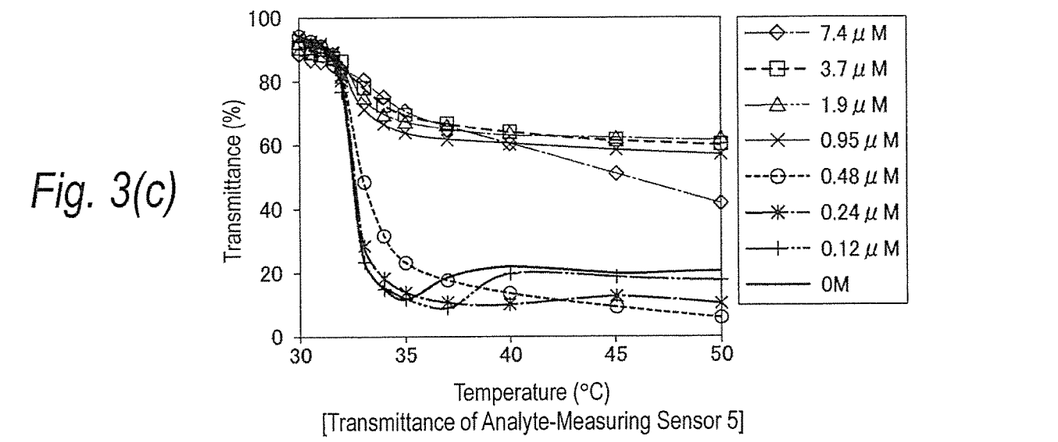
FIG. 3C is a graph showing the relationship between the temperature and the transmittance when the avidin concentration of Analyte-Measuring Sensor 5 is varied.
Figure 4A:
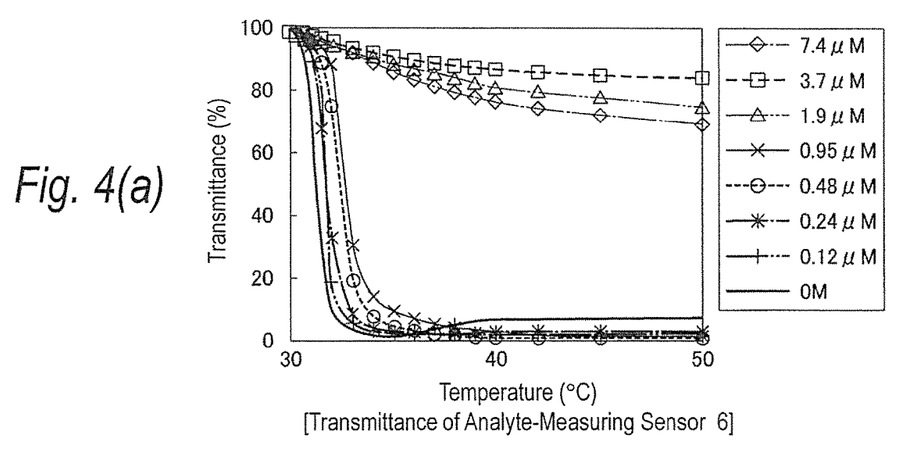
FIG. 4A is a graph showing the relationship between the temperature and the transmittance when the avidin concentration of Analyte-Measuring Sensor 6 is varied.
Figure 4B:
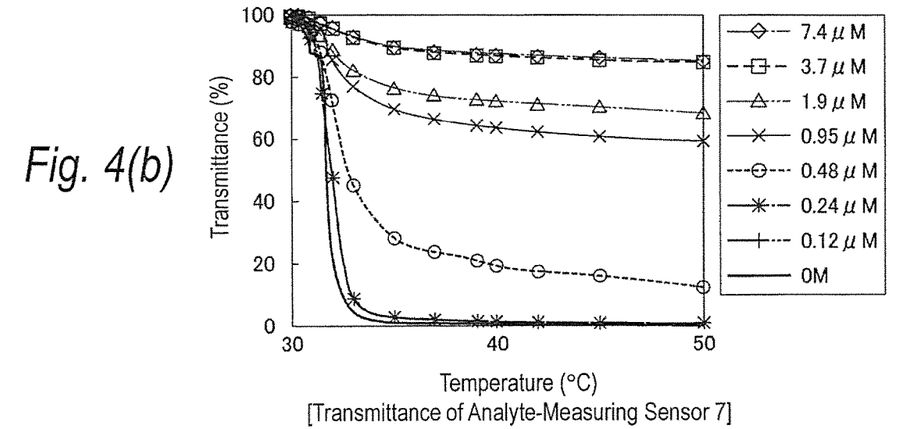
FIG. 4B is a graph showing the relationship between the temperature and the transmittance when the avidin concentration of Analyte-Measuring Sensor 7 is varied.
Figure 4C:
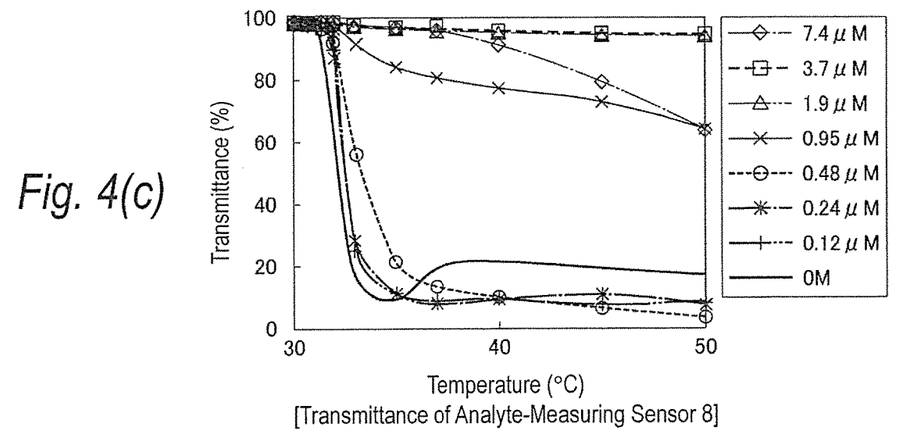
FIG. 4C is a graph showing the relationship between the temperature and the transmittance when the avidin concentration of Analyte-Measuring Sensor 8 is varied.

[Measurement Conditions]
Particle diameter of metal particle: 13 nm
Concentration of metal particle solution: 0.027 g-Au/L
Polymer concentration: 0.0625 mass %
Measurement temperature: 20° C.
Wavelength: 850 nm
Standard solution: pure water In addition, with regard to the analyte-measuring sensor solution prepared above (Analyte-Measuring Sensors 1 and 2), the transmittance when changing the temperature was measured by using a solution in which the avidin concentration was varied in the range of from 0 to 7.4 μmol. The measurement conditions are as follows. FIG. 2A and FIG. 2B show the change in the transmittance of the solution due to change in the avidin concentration.

[Measurement Conditions]
Particle diameter of metal particle: 13 μm
Concentration of metal particle solution: 0.0162 g-Au/L
Polymer concentration: 0.0625 mass %
Biotinated sodium polyacrylate concentration: 0.22 mg/mL
Measurement wavelength: 850 nm
Standard solution: pure water From the results of FIG. 2A and FIG. 2B, it was understood that the presence or absence of avidin produces a difference in the transmittance curve. This indicated that the analyte-measuring sensor of the present invention is suitable for the detection of avidin. Among others, in the case of Analyte-Measuring Sensor 1, avidin yielded a large difference in the transmittance curve and was found to exhibit good conjugation efficiency to the analyte-measuring sensor.

Test Example 3: Particle Diameter of Metal Particle and Biotin Introduction Ratio Each of the metal particles having a particle diameter of about 13 nm and about 30 nm produced in Test Example 1 was conjugated using three kinds of three-component copolymers (terpolymer) differing in the biotin introduction ratio (biotin introduction ratio: 0.125 mol %, 0.25 mol %, 0.375 mol %) to prepare six kinds of Analyte-Measuring Sensors 3 to 8. That is, two kinds of metal particles differing in the particle diameter (13 nm and 30 nm) prepared according to the procedure above in Preparation of Metal Particle Solution and three kinds of three-component copolymers NIP- TETA-Bio differing in the biotin introduction ratio synthesized according to the synthesis procedure of NIP-TETA-Bio above (biotin introduction ratio: 0.125 mol %, 0.25 mol %, 0.375 mol %) were used.

To a 50 mL measuring flask, 6.25 mL of a 2.0 mass % NIP-TETA-Bio solution (biotin introduction ratio: 0.125 mol %, 0.25 mol %, 0.375 mol %) and 15 mL of a 0.18 g-Au/L metal particle solution (particle diameter: about 13 nm, 30 nm) were added and diluted with pure water to adjust the volume to 50 mL.

The resulting solution was heated at 90° C. for 30 minutes by means of a water bath, cooled at 0° C. for 30 minutes by means of an ice bath, and stirred. This operation was repeated three times. The obtained solution was put in a cellophane tube with a molecular weight cut off of 10,000, the tube was immersed in a 1 L beaker filled with pure water, and dialysis was carried out for 5 days by replacing the pure water every day.

The particle diameter of the metal particle and the biotin introduction ratio in the terpolymer of each of Analyte-Measuring Sensors 3 to 8 are shown in Table 1.

TABLE 1

| No. | Particle Diameter of Metal Particle (nm) | Biotin Introduction Ratio in Terpolymer (mol %) |
|---|---|---|
| Analyte-Measuring Sensor 3 | 13 | 0.125 |
| Analyte-Measuring Sensor 4 | 13 | 0.25 |
| Analyte-Measuring Sensor 5 | 13 | 0.375 |
| Analyte-Measuring Sensor 6 | 30 | 0.125 |
| Analyte-Measuring Sensor 7 | 30 | 0.25 |
| Analyte-Measuring Sensor 8 | 30 | 0.375 |

With regard to Analyte-Measuring Sensors 3 to 8, the transmittance of the solution was measured according to the method in Measurement of Transmittance above by changing the concentration of added avidin in the range of from 0 to 7.4 μmol. The measurement conditions are as follows. FIG. 3A to FIG. 3C and FIG. 4A to FIG. 4C show the change in the transmittance of the solution due to change in the avidin concentration.

Figure 5A:
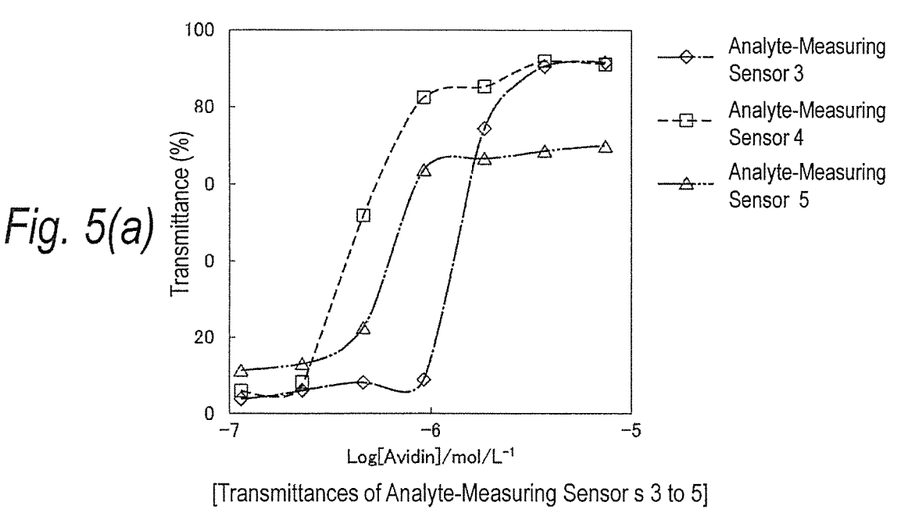
FIG. 5A is a graph showing the results of Analyte-Measuring Sensors 3 to 5.
Figure 5B:
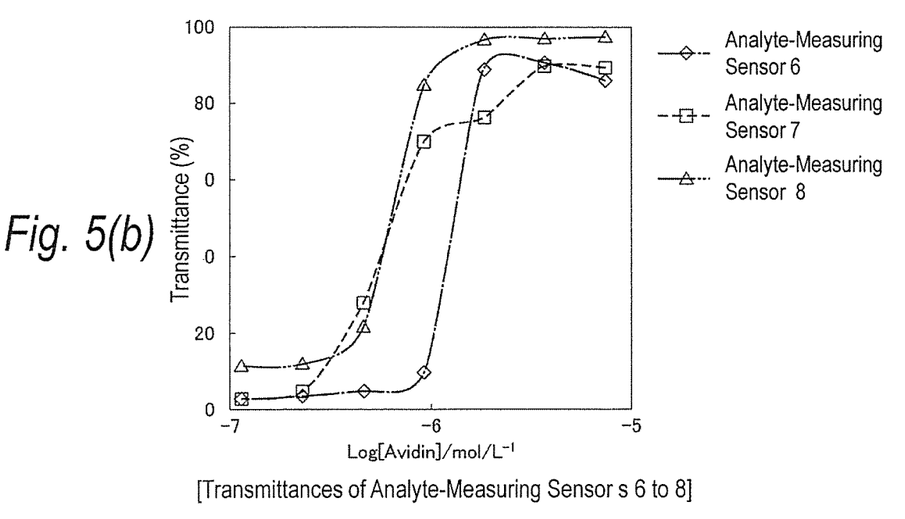
FIG. 5B is a graph showing the results of Analyte-Measuring Sensors 6 to 8.

In addition, FIG. 5A and FIG. 5B show the relationship between the avidin concentration and the transmittance at 35° C. when using respective analyte-measuring sensors. FIG. 5A shows the results of Analyte-Measuring Sensors 3 to 5 using a metal particle of 13 nm, and FIG. 5B shows the results of Analyte-Measuring Sensors 6 to 8 using a metal particle of 30 nm.

[Measurement Conditions]
Concentration of metal particle solution: 0.0162 g-Au/L
Polymer concentration: 0.0625 mass %
Biotinated sodium polyacrylate concentration: 0.22 mg/mL
Measurement wavelength: 850 nm
Standard solution: pure water It was understood from the results in FIG. 3A to FIG. 3C, FIG. 4A to FIG. 4C, FIG. 5A and FIG. 5B that with use of any analyte-measuring sensor, the profile of the transmittance curve is changed according to the avidin concentration at a temperature not less than the phase transition temperature of the analyte-measuring sensor.

Test Example 4: Transmittance of Analyte-Measuring Sensor Solution

To a quartz-made semi-microcell having a light path length of 1 cm, 300 μL of Analyte-Measuring Sensor 4, 100 μL of a 7.4 μmol/L avidin solution and 50 μL of a 8.0 μmol/L biotinated sodium polyacrylate solution were sequentially added, and 450 μL of pure water and 100 μL of PBS were added to afford a final liquid amount of 1 mL (Example 1).

Aqueous solutions adjusted to a final volume of 1 mL were produced in the same manner by using 1) 300 μL of an analyte-measuring sensor solution (Analyte-Measuring Sensor 4), 2) 300 μL of an analyte-measuring sensor solution (Analyte-Measuring Sensor 4) and 50 μL of a biotinated sodium polyacrylate solution, or 3) 300 μL of an analyte-measuring sensor solution (Analyte-Measuring Sensor 4) and 100 μL of an avidin solution (Comparative Examples 1 and 2 and Reference Example 1).

The configurations of measurement solutions of Example 1, Comparative Examples 1 and 2 and Reference Example 1 are shown in Table 2.

TABLE 2

| | Configuration of Measurement Solution | | |
|---|---|---|---|
| | Analyte-Measuring Sensor 4 | Avidin Solution | Biotinated Sodium Polyacrylate Solution |
| Example 1 | 300 μL | 100 μL | 50 μL |
| Comparative Example 1 | 300 μL | — | — |
| Comparative Example 2 | 300 μL | — | 50 μL |
| Reference Example 1 | 300 μL | 100 μL | — |

Figure 6:
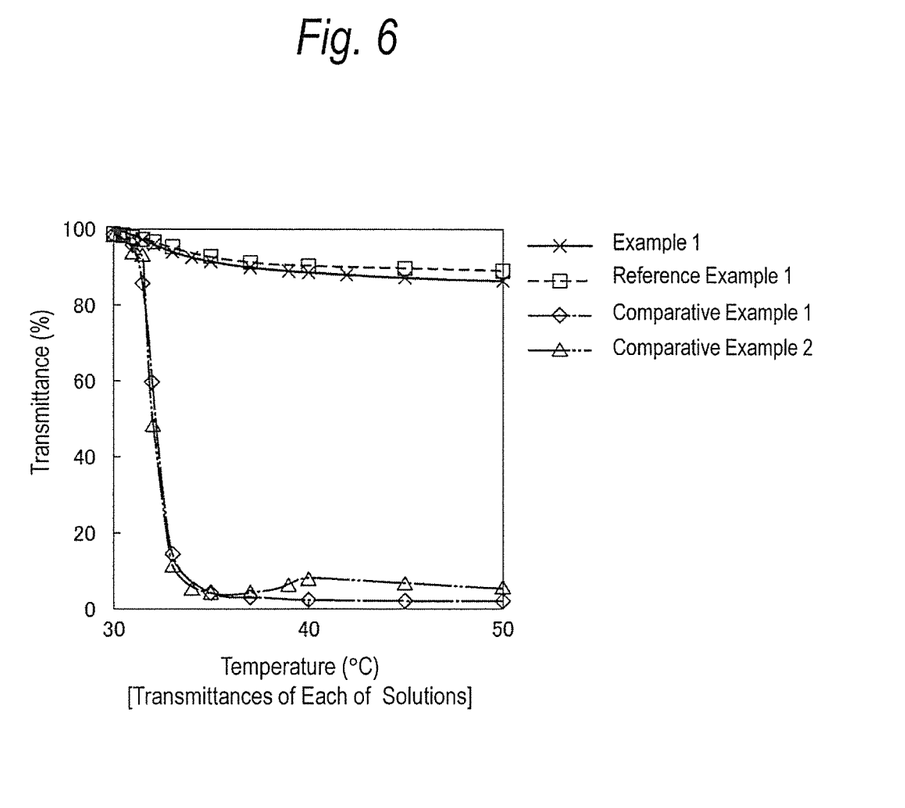
FIG. 6 is a graph showing the relationship between the temperature and the transmittance when each of avidin and a thermoresponsive polymer is present or absent.

The measurement solution produced was lightly stirred by hand and after each sample solution was made uniform, the transmittance was measured at a wavelength of 850 nm by changing the temperature. The measurement conditions are as follows. FIG. 6 shows the results.

[Measurement Conditions]
Particle diameter of metal particle: 13 nm
Concentration of metal particle solution: 0.0162 g-Au/L
Polymer concentration: 0.0625 mass %
Biotinated sodium polyacrylate concentration: 0.22 mg/mL
Measurement wavelength: 850 nm
Standard solution: pure water As seen from the results of FIG. 6, in Comparative Examples 1 and 2, the transmittance was reduced at a temperature not lower than the phase transition temperature (LCST or more) of the solution. This is considered to be attributable to the fact that phase transition occurs due to absence of avidin to involve hydrophobization of the thermoresponsive polymer constituting the analyte-measuring sensor, leading to reduction in the solubility, and an electrostatic interaction in the system of analyte-measuring sensor and biotinated sodium acrylate causes cancellation of the charge, leading to reduction in the solubility. On the other hand, in Example 1, similarly to Reference Example 1, the transmittance showed a high value even at a temperature not lower than the phase transition temperature (LCST or more) of the solution. This is considered to be attributable to the fact that an interaction of analyte-measuring sensors with each other through avidin or of an analyte-measuring sensor with biotinated sodium polyacrylate imposes a steric restriction between the charged substance (TETA) polymerized with the thermoresponsive polymer and the charge group (polyanion) of sodium polyacrylate and the hydrophobicity of the system is thereby maintained.

Test Example 5: Transmittance of Analyte-Measuring Sensor Under Condition of Coexistence of Bovine Serum Matrix With regard to Analyte-Measuring Sensor 4, the transmittance when changing the temperature was measured by adding a 10 vol % bovine serum solution (Bovine Serum, produced by GIBCO), an avidin solution having a concentration of 0 to 7.4 μmol/L, a 4.4 mg/mL biotinated sodium polyacrylate solution, and Working Buffer.

Figure 7:
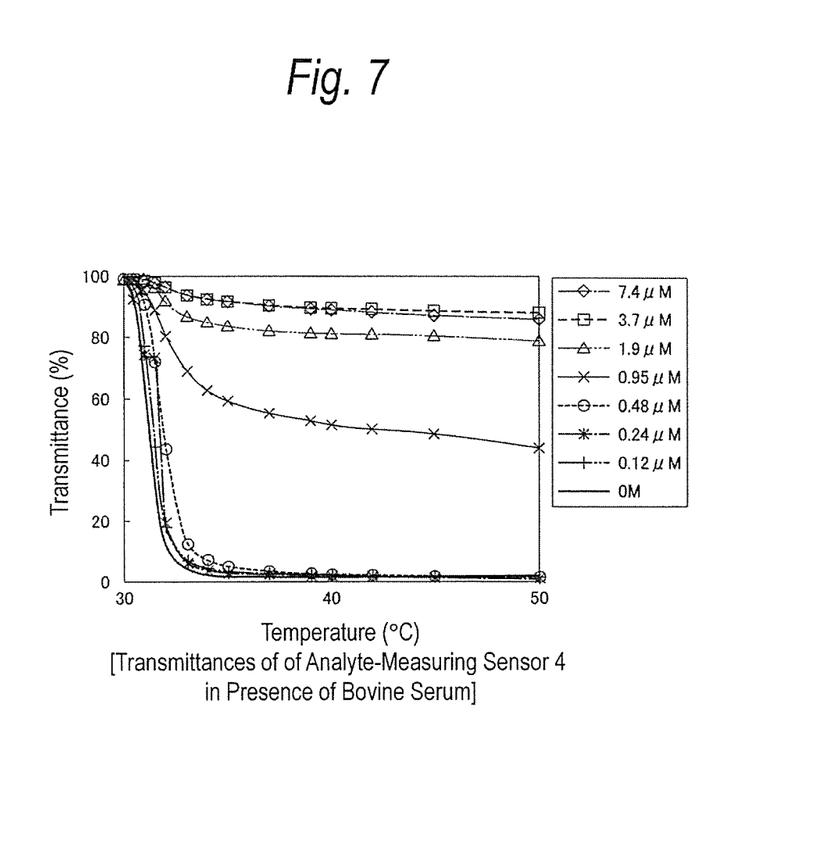
FIG. 7 is a graph showing the relationship between the temperature and the transmittance when the avidin concentration of Analyte-Measuring Sensor 4 is varied under the condition that a bovine serum matrix is coexistent.

To a quartz-made semi-microcell having a light path length of 1 cm, 300 μL of the analyte-measuring sensor solution, 25 μL of the 10 vol % bovine serum solution, 100 μL of the avidin solution and 50 μL of the biotinated sodium polyacrylate solution were sequentially added. Subsequently, 425 μL of pure water and 100 μL of Working Buffer were added to afford a final liquid amount of 1 mL. The resulting solution was lightly stirred by hand and after each sample solution was made uniform, the transmittance was measured at a wavelength of 850 nm. The measurement conditions are as follows. FIG. 7 shows the change in the transmittance of the solution due to change in the avidin concentration.

<Composition of Working Buffer>
0.5 w/v % Bovine Albumin
0.5 w/v % TritonX-100
10 mmol/L EDTA
NaCl 0.014 mol/L
KCl 0.003 mol/L
$NaH_2PO_4$ 0.008 mol/L
$KH_2PO_4$ 0.002 mol/L

[Measurement Conditions]
Particle diameter of metal particle: 13 nm
Concentration of metal particle solution: 0.0162 g-Au/L
Polymer concentration: 0.0625 mass %
Biotinated sodium polyacrylate concentration: 0.22 mg/mL
Bovine serum concentration: 0.25 vol %
Measurement wavelength: 850 nm
Standard solution: pure water Next, measurement of avidin was carried out in the presence of a bovine serum matrix.

With regard to Analyte-Measuring Sensor 4, DLS measurement was carried out by adding an avidin solution having a concentration of 0 to 7.4 μmol/L, a 4.4 mg/mL biotinated sodium polyacrylate solution, and PBS.

Figure 8:
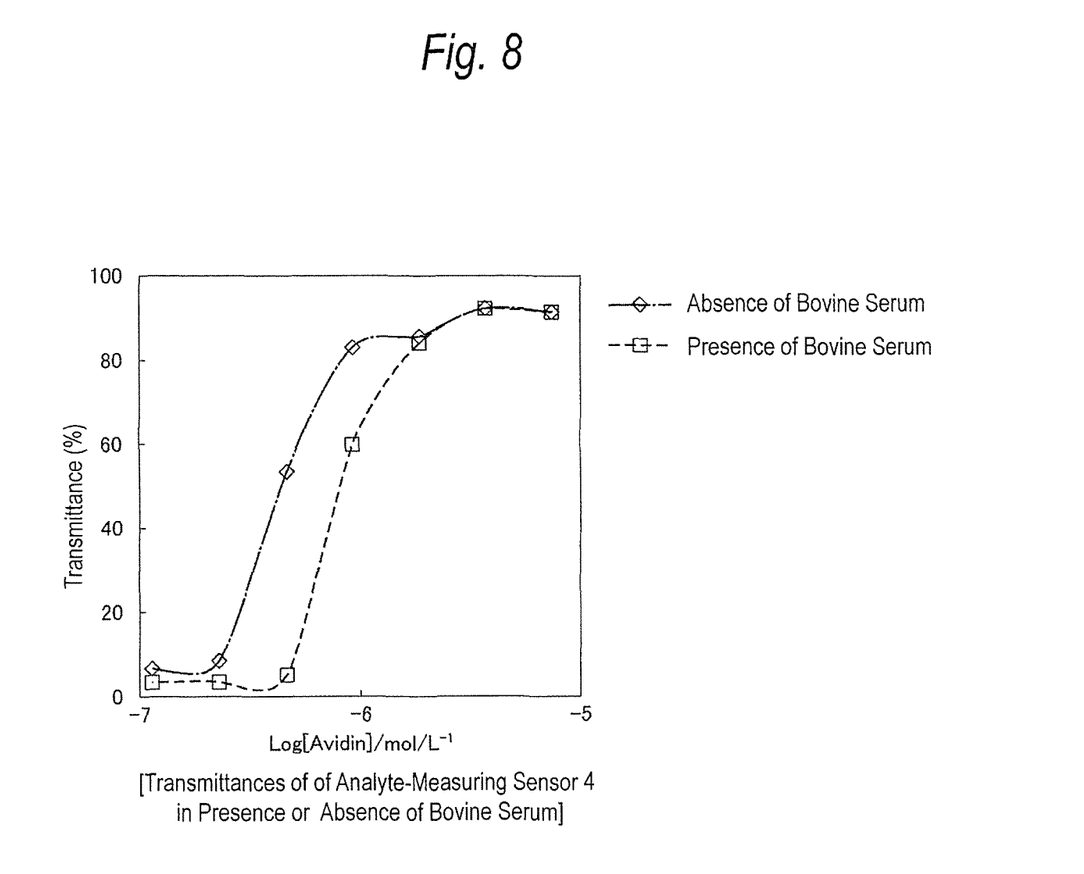
FIG. 8 is a graph showing the relationship between the avidin concentration and the transmittance at 35° C. of Analyte-Measuring Sensor 4 in the presence or absence of a bovine serum matrix.

To a glass cell, 600 μL of a gold nanoconjugate solution, 200 μL of the avidin solution, and 100 μL of the biotinated polyacrylate solution were sequentially added. Subsequently, 900 μL of pure water and 200 μL of a PBS solution were added to afford a final liquid amount of 2 mL. The resulting solution was lightly stirred by hand and after each sample solution was made uniform, DLS measurement was carried out at 30° C. and 40° C. that are a temperature around the phase transition temperature of the gold nanoconjugate solution. Three sets were measured for one sample by automatic measurement. The measurement conditions are as follows. FIG. 8 shows the relationship between the avidin concentration and the transmittance at 35° C. in the presence or absence of a bovine serum matrix.

[Measurement Conditions]
Particle diameter of metal particle: 13 nm
Concentration of metal particle solution: 0.0162 g-Au/L
Polymer concentration: 0.0625 mass %
Biotinated sodium polyacrylate concentration: 0.22 mg/mL
Bovine serum concentration: 0.25 vol %
Measurement temperature: 35° C.
Measurement wavelength: 850 nm
Standard solution: pure water As seen from the results of FIGS. 7 and 8, the detection sensitivity is slightly reduced when bovine serum is present together, but a similar S-shaped phase transition curve is yielded irrespective of presence or absence of bovine serum. This indicates that the analyte-measuring sensor can be applied to measurement of a measurement target analyte by performing matrix matching.

While the invention has been described in detail and with reference to specific embodiments thereof, it will be apparent to one skill in the art that various changes and modifications can be made therein without departing from the sprit and scope thereof. This application is based on Japanese patent application No. 2012-194085 filed on Sep. 4, 2012, the entire contents of which are incorporated hereinto by reference.

EXPLANATIONS OF REFERENCE SIGNS

1: Analyte-Measuring Sensor
2: Measurement target analyte
3: Conjugated compound
11: Metal particle
12: Thermoresponsive polymer
13: Charged substance
14, 15: Labeled particle

The invention claimed is:

1. An analyte-measuring sensor comprising:
a copolymer, obtained by copolymerizing:
a particle capable of specifically reacting with an analyte;
a thermoresponsive polymer, wherein a monomer of the thermoresponsive polymer is at least one of N-isopropylacrylamide or vinyl methyl ether; and
a reaction intermediate of reacting a charged substance exhibiting a positive zeta potential in an aqueous solution with acryloyl chloride, wherein the reaction intermediate is selected from the group consisting of acryloyl triethylenetetramine, acryloyl tetraethylenepentamine, and acryloyl pentaethylenehexamine,
wherein functional groups of the particle capable of specifically reacting with an analyte, the thermoresponsive polymer, and the reaction intermediate are located on side chains of the copolymer; and
a metal particle,
wherein said metal particle is coated with the copolymer.

2. The analyte-measuring sensor as claimed in claim 1, wherein an average particle diameter of said metal particle is from 10 to 50 nm.

3. The analyte-measuring sensor as claimed in claim 1, wherein said metal particle comprises gold (Au), silver (Ag), platinum (Pt) or palladium (Pd).

4. The analyte-measuring sensor as claimed in claim 1, wherein said thermoresponsive polymer is at least one of poly(N-isopropylacrylamide) or poly(vinyl methyl ether).

5. The analyte-measuring sensor as claimed in claim 1, wherein said particle is selected from the group consisting of an antibody, an antigen, peptide, a single-strand DNA, a single-strand RNA, and a functional derivative thereof.

6. The analyte-measuring sensor as claimed in claim 1, wherein said thennoresponsive polymer has an amino group.

7. The analyte-measuring sensor as claimed in claim 1, which contains said particle in an amount of 0.1 to 0.4 mass %.

* * * * *